US006268191B1

(12) United States Patent
Prud'homme et al.

(10) Patent No.: US 6,268,191 B1
(45) Date of Patent: Jul. 31, 2001

(54) ENZYME IMMOBILIZATION BY IMBIBING AN ENZYME SOLUTION INTO DEHYDRATED HYDROCOLLOID GEL BEADS

(76) Inventors: Robert K. Prud'homme, 61 Lillie St., Princeton Junction, NJ (US) 08550; Catherine-Ann Cukras, Apt. E, 5391 Pershing Ave., St. Louis, MO (US) 63112-1787; Henry A. Pfeffer, 6 Hollyhock Way, Hamilton, NJ (US) 08619

( * ) Notice: Subject to any disclaimer, the term of this patent is extended or adjusted under 35 U.S.C. 154(b) by 0 days.

(21) Appl. No.: 09/395,465

(22) Filed: Sep. 14, 1999

Related U.S. Application Data

(60) Provisional application No. 60/101,210, filed on Sep. 21, 1998.

(51) Int. Cl.$^7$ ............... C12N 11/10; C12N 11/04; C12N 9/98; C12N 9/96; C12P 7/62
(52) U.S. Cl. ............... 435/178; 435/41; 435/135; 435/182; 435/187; 435/188
(58) Field of Search ............... 435/177, 178, 435/182, 41, 135, 187, 188

(56) References Cited

U.S. PATENT DOCUMENTS

| 4,182,655 | 1/1980 | Hartmeier ............... 435/181 |
| 4,975,375 | 12/1990 | Haruta et al. ............... 435/182 |
| 5,662,840 | 9/1997 | Thomas et al. ............... 264/12 |

OTHER PUBLICATIONS

Pantiliano et al., "Large increases in General Stability for Subtilsin BPN' through Incremental Changes in The Free Energy of Unfolding", Biochemistry vol. 28, pp. 7205–7213 (1989).
Guide to Protein Purification, "Methods in Enzymology", vol. 182 pp. 77–78, The Academic Press, Inc. 1990.
Moon et al., "Characterization of k–Carrageenen Gels Used for Immobilization of Bacillus firmus", Biotechnol. Prog., vol. 7 (6) pp. 518–525 (1991).
Chen et al., "Enzyme Engineering for Nonaqueous Solvents. II. Additive effects of Mutations on the Stability and Activity of Subtilsin E in Polar Organic Media", Biotechnol Prog., vol. 7 125–129 (1991).
Enzyme Catalysis in Organic Synthesis, A comprehensive Handbook, pp. 74–87, 1993.
Volkin et al., "Enzyme Thermoinactivation in Anhydrous Organic Solvents", Biotech. and Bioeng., vol. 37 pp. 843–853 (1991).
Arnaud et al., "Diffusion of Lactose in k–Carrageenan/ Locust Bean Gum Gel Beads with or without Entrapped growing lactic acid bacteria", Biotech. and Bioeng., vol. 38, pp. 1041–1049 (1991).
Chatterjee et al., "Determination of Equilibrium and individual rate constants for subtilsin–catalyzed Transesterification in Anhydrous environments", Biotech. and Bioeng., vol. 40, pp. 1069–1077 (1992).
Xu et al., "Engineering subtilsin for use in Organic solvents", vol. 672, pp. 94–99 (1992).
Adams et al., "Kinetic Isotope effect investigation of enzyme mechanism in organic solvents", vol. 112 pp. 9418–9419 (1990).
Klibanov et al., "Enzymatic catalysis in anhydrous organic solvents" TIBS 14, pp. 141–144 (1989).
Klibanov et al., Asymmetric Transformations catalyzed by enzymes in organic solvents, Acc. Chem. Res., vol. 23 pp. 114–120 (1990).
Oakenfull et al., "A kinetic investigation of the extent of polymer aggreration in carregeenan and Gels", Chemistry and Industry, pp. 201–202 (1987).
Ryan et al. "Immoblization of Escherichia coli JM103 [pUC8] in k–Carrageenan coupled with recombinant Protein release by in Situ cell membrane permeabilization", Biotechnol. Prog., vol. 7, pp. 99–110 (1991).
Waagikar et al., "Protein and Solvent engineering of Subtilsin BPN' in nearly Anhydrous Organic Media", Journal of the American Chem. Soc., vol. 115 pp. 12231–12237 (1993).
Zaks et al., Enzymatic Catalysts in nonaqueous solvents, Joun. Of Bio. Che., vol. 263 (7) pp. 3194–(1988).

*Primary Examiner*—David M. Naff
(74) *Attorney, Agent, or Firm*—Bruce M. Monroe; Robert L. Anderson; Patrick C. Baker

(57) ABSTRACT

Enzymes are immobilized for use in non-aqueous enzymatic reactions by dehydrating hydrocolloid gel beads having an average particle size of 5 to 150 microns and a network structure capable of swelling in aqueous media, immersing or suspending the dehyrated gel beads in an aqueous solution of enzyme where the beads swell and imbibe the enzyme solution, optionally dehydrating the resultant enzyme-containing gel beads and recovering the gel beads containing the enzyme. In a specific method, the hydrocolloid is carrageenan such a kappa carragennan, the enzyme is subtilisin Carlsberg, the aqueous enzyme solution contains 0.05% to 40 wt % enzyme and the amount of enzyme imbibed is 0.05 to 0.5 grams of enzyme per gram of dehydrated gel beads.

18 Claims, No Drawings

ENZYME IMMOBILIZATION BY IMBIBING AN ENZYME SOLUTION INTO DEHYDRATED HYDROCOLLOID GEL BEADS

This invention claims the benefit of U.S. Provisional Application No. 60/101,210, filed Sep. 21, 1998.

BACKGROUND OF THE INVENTION

This invention is directed to physically immobilizing enzymes for use in non-aqueous enzymatic reactions.

The motivation for using enzymes in organic environments, which are completely unlike their natural uses in an aqueous environment, is predominantly for industrial applications. Pharmaceutical companies, in particular, have an interest in using enzymes in non-aqueous environments since most drug synthesis is performed in organic solvents. One particularly desirable application for the use of enyzmes in organic media is catalyzing stereospecific reactions where only one isomer is useful out of several possible isomers. Enzymes are limited in their ability to function effectively as catalysts in organic media, are generally useful in catalyzing only specific reactions, and generally are useful only at relatively low temperatures and pressures. Therefore there is a need to improve the ability to employ enzymes to conquer these problems and facilitate the use of various enzymes in organic reactions.

Immobilization of enzymes is important in industrial application. When enzymes are used in reactors they must be "immobilized" so that they can be separated from the product, recovered, and recycled. Immobilization of enzymes on supports in aqueous media is widely practiced. The literature also describes the covalent attachment of enzymes to inorganic and organic surfaces, membranes and gels. Work has also been performed on physically entrapping enzymes in membranes and gels. Successful industrial implementation of non-aqueous enzymology will require new approaches for immobilizing enzymes in organic media without compromising their activity.

Substantial literature exists relating to non-aqueous enzymology, expecially in the examination of the kinetics of anhydrous enzymes in various organic solvents under varied reactions conditions. Issues have been described such as the increased thermal stability of enzyme(s) in organic solvents which have been attributed to the high kintic barriers preventing protein unfolding, altered substrate specificity, and the ability of these enzymes to catalyze novel reactions in this media. The requirements of the enzyme for water in organic solvents has also been examined.

The recovery and reuse of nonimmobilized enzymes has been of substantial difficulty in the art to present. Using currently available techniques of enzyme recovery, either the method of removal contaminated the enzyme, which renders the enzyme useless for reuse, or the activity of the enzyme is destroyed in the recovery process. In either case, removing the biofunctional enzyme from a reaction mixture which it catalyzes has proved difficult. In addition, when using a dry enzyme in an organic solvent, not only must the difficulty of removal be confronted, but also the enzyme's tendency to agglomerate, which results in a reduction of the surface area available to catalyze the reaction, thereby significantly slowing the rate of reaction. Each of these problems must be considered when attempting to recover intact enzymes from nonaqueous environments.

Methods of enzyme immobilization which have been discussed in the literature include: covalent binding, non-covalent binding, and physical entrapment. Immobilizing enzymes by covalently bonding them to a carrier has the advantage that the enzyme is prevented from leaking from the carrier regardless of the stringency of the conditions. However, this form of immobilization has the disadvantage that it generally alters the conformational structure and reactivity of the active site. Non-covalent bonds such as hydrophobic binding, polar binding electrostatic interactions and hydrogen bridge binding (adsorption) have been used to associate the enzyme with a carrier material without forming covalent bonds. Since the binding is not as strong as covalent bonding, the conformation of the enzyme is usually not significantly altered and therefore the reactivity of the enzyme is not severely reduced. However, this weaker binding also leaves the possibility for the enzyme to leak from the carrier more easily. Entrapment of the enzyme does not involve any type of chemical binding, but instead only physically restricts the enzyme's movement within a polymer matrix. It therefore does not interfere with the enzyme conformation at all. However, depending on the method of entrapment, the enzyme may be damaged if polymer conditions are more stringent or may simply be occluded so that its reactivity is reduced.

Recent research on entrapment has been performed using kappa-carrageenan as the polymer matrix for immobilizing both cells and enzymes. κ-carrageenan is a linear polysaccharide made up of alternating 1,3-linked B-D-galactose-4-sulfate and 1-4-linked 3,6-anhydr-α-D-galactose as shown in figure 1.

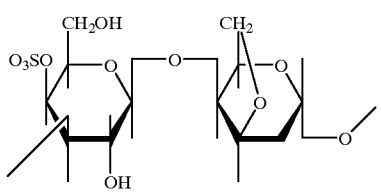

Figure 1

This polymer forms a gel network in two steps. The first step involves the partial association of polymer chains into double helices. The association of helices into "domains" by the addition of a cation (usually potassium) produces the gel network. The gelation temperatures of κ-carrageenan polymers are reported to be dependent on the cation concentration, and relatively independent of carrageenan concentration. The most common method used to immobilize biological cell suspensions in carrageenan gels is to prepare a carrageenan solution in the absence of cations, and when the solution has cooled to about 45° C. the cell suspension is added and the gel is configured into the desired geometry. Once the gel has cooled, it is cured with a KCl solution. Moon et al (Biotechnol. Proc., 7, 516 (1991)) also attempted to immobilize cells by diffusing them into pre-formed gels. These gels were cured with KCl solution and post-crosslinked to prevent cell leakage. However, cell viability was destroyed during this process.

SUMMARY OF THE INVENTION

This present invention provides a method for immobilizing an enzyme for use as a catalyst in organic reactions by imbibing an enzyme into a dehydrated hydrocolloid polymer gel bead. More particularly, the invention comprises the steps of (a) dehydrating a hydrocolloid gel bead having an average particle size in the range of 5 µm 150 µm in diameter, (b) imbibing into the dehydrated hydrocolloid gel bead an aqueous solution of the enzyme to form an imbibed gel bead; and (c) optionally dehydrating the imbibed gel bead, recovering a gel bead in which a catalytically effective amount of enzyme has been immobilized. The enzyme may be an oxidoreductase, transferase, hydrolase, lyase, isomerase, ligase, decarboxylase, carboxylase, aldolase, thiolase, or synthase. In a particularly preferred embodiment, the hydrocolloid is carrageenan or kappa carrageenan. One preferred enzyme is subtilisin Carlsberg. In a particularly preferred embodiment, the hydrocolloid is carrageenan and the enzyme is subtilisin Carlsberg, in which the aqueous solution of enzyme contains in the range of 0.05 to 40 wt % enzyme. A preferred method of dehydration is lyophilization. The invention also provides a gel bead in which an enzyme has been immobilized by the foregoing process.

DETAILED DESCRIPTION

In accordance with one aspect of the present invention, there is provided a process for immobilizing enzymes for use in catalyzation of organic reaction systems, in which the enzyme is imbibed in a dehydrated bead of a bead-forming hydrocolloid polymer.

The bead-forming polymers suitable for use in the present invention include various hydrocolloids which gel upon cooling. Carrageenan, preferably kappa caragenan which is described generally above, and other polymers which are capable of being formed into gel beads which have a network structure capable of imbibing or entrapping enzymes are suitable for use in the present invention. In addition it is highly beneficial that the dehydrated beads are capable of swelling in the presence of aqueous solutions or suspensions of the enzyme to facilitate imbibition of the enzyme into the dried bead. Other polymers which may be suitable for use in the present invention include agars, agaroses, algins, low methoxyl pectins, gellans, furcellaran, curdlan, chitosan, konjac glucomannan and various derivatives thereof, and mixtures of two or more of the foregoing, as well as hydrocolloid mixtures such xanthan/locust bean gum, locust bean gum/agar, cassia/agar, cassia/xanthan, konjac/xanthan, carrageenan/locust bean gum, konjac/carrageenan, and konjac/starch. Carrageenan is particularly desirable as the hydrocolloid polymer due to its networked structure, its ability to form very fine particle size beads, its ability to swell in aqueous media and its ability to interact with proteins.

Use of a small diameter bead of 20 $\mu$m or less is believed to minimize diffusion resistance and thereby facilitate imbibition and immobilization of enzymes carried in aqueous media, as well as promote availability of the enzyme at the active site. However, beads having an average diameter in the range of 5 to 150 microns, more preferabiliy 5 to 50 $\mu$m may be employed.

The polymer beads may be prepared by methods known in the art. Particularly desirable are the very fine gel beads formed according to the process described in U.S. Pat. No. 5,662,840, which is incorporated herein by reference, in which a hydrocolloid sol, such as carrageenan, is intimately contacted with sufficient atomizing gas to immediately flash cool the sol to a temperature below the gellation temperature of the sol. This method has the advantage of producing very fine uniform gel beads having an average diameter in the range of about 5 to 50 microns, preferably in the range of 10 up to about 20 microns.

Nearly all enzymes are suitable for use in this invention. Preferred enzymes suitable for use in the present invention include oxidoreductases (including but not limited to, dehydrogenases, oxidases, reductases, hydroxylases, monooxygenases, peroxidases, and nitrogenases), transferases (including but not limited to, proteases, esterases, aminotransferases, phosphatases, nucleases, phosphodiesterases, and phosphorlases), hydrolases, lyases (including but not limited to, aconitase, fumarase, enolases, crotonase, dehydrases, and aspartase), isomerases (including but not limited to racemases, epimerases, and mutases), and ligases (including but not limited to synthetases and carboligase). Additional preferred enzymes suitable for the present invention include, but are not limited to, decarboxylases, carboxylases, aldolases, thiolases, and synthases. The present invention is illustrated utilizing subtilisin Carlsberg as the enzyme.

The immobilization technique involves imbibing the enzyme into pre-formed hydrocolloid beads. The beads are suitably manufactured utilizing a carrageenan mixture containing from about 0.5 to about 4 wt %, preferably about 2 wt % carrageenan, 0.05 to about 0.4 wt %, preferably about 0.2 wt % potassium chloride, 0.025 to about 0.2 wt %, preferably about 0.1 wt % calcium chloride, and 0.025 to about 0.2 wt %, preferably about 0.1 wt % sodium benzoate in deionized water The resultant beads are then dehydrated. The method of dehydration is not critical, and any suitable method may be employed. A convenient and preferred method is lyophilization which may be conducted on either a laboratory or large scale, using the techniques described generally in *Methods in Enzymology, "Guide to Protein Purification"*, V. 182, pp. 77–8, Academic Press, Inc. Large scale lyophilizations are useful in carrying out the present invention commercially and are well known to those skilled in the art. Regardless of scale, lyophilization involves the rapid freezing of the microbeads and subsequent removal of the water contained therein by sublimation under a vacuum. An alternative method of dehydration involves contacting the gel microbeads with a water miscible alcohol, e.g., ethanol or isopropanol.

Following dehydration, the enzyme is imbibed in the dried beads from an enzyme solution. This imbibition step generally involves immersing or suspending the dried beads in an aqueous solution of the enzyme, preferably with stirring or agitation, for a period of time sufficient to permit the beads to swell in the aqueous solution and to allow the entrained enzyme to bind to the pre-formed bead, generally in the range of 0.5 to 8 hours. The amount of solution used for swelling and the concentration in the solution will vary depending on the polymer employed for the bead and on the enzyme being employed. In general the amount of aqueous enzyme solution employed should be equal to or in excess of the moisture loss on lyophilization of the gel bead; it should be sufficient to restore the bead to a fully hydrated condition. Excess solution and excess enzyme, for example up to a 50% excess, is desirably employed to maximize the amount of enzyme imbibed into the bead. For the carrageenan beads employed to illustrate this invention the amount of solution was calculated to be enough to swell the gel bead to its original (pre lyophilized) moisture content of about 2 wt % plus an extra 50% of this amount. The amount of enzyme employed may be in the range of 0.05 to about 0.5 gram of enzyme per gram of carrageenan for subtilisin Carlsberg, preferably about 0.25g of enzyme per gram of carrageenan (0.2g per gram of dried carrageenan). The aqueous solution may suitably contain from about 0.05 wt % to about 40 wt % enzyme, preferably about 0.05 wt % to about 5 wt %, more preferably about 0.05wt %.

Depending on the enzyme, the aqueous solution of enzyme may also contain compatible water-soluble buffers and stabilizers, particularly for those enzymes whose activity and/or ability to bind to the gel bead is pH dependent. For example, for the enzyme subtilisin Carlsberg, it is advantageous to employ a pH of about 7.8, advantageously a 20 mM potassium phosphate buffer adjusted to pH of 7.8 with KOH.

It is well known to those skilled in the art that an increase in polarity of the enzyme can improve the catalytic activity of the enzyme in organic solvents. This increase in polarity may be accomplished by assuring that a small amount of water is in intimate contact with the wildtype enzyme. With subtilisin Carlsberg, for example, it is desirable to have water present at a level equal to about 10 ul/mg of enzyme in order to maximize the activity of this enzyme. In general, this amount of water is obtained by utilizing an aqueous solution of the enzyme for imbibation of the enzyme, and can be altered by controlling the amount of dehydration or adding additional water to the organic reaction medium. Alternatively, the increase in polarity of the active site of the enzyme may be achieved by genetically engineering the enzyme to directly alter the polarity of the active site. In one embodiment of the present invention with subtilisin Carlsberg as the enzyme, water is present in the range of 10 ul/mg and the pH is adjusted to 7.8.

Following imbibition as generally described above, the excess liquid is then removed from the beads by any suitable means, for example by centrifugation or decantation. The beads may then be recovered and used as such or further dehydrated and stored or shipped for later use. The beads may be lyophilized or otherwise dehydrated in the manner described above to provide a dehydrated gel bead in which a catalytically effective amount of enzyme has been immobilized.

The following examples demonstrate, by way of illustration but not of limitation, the method of the present invention utilizing carrageenan bead and the enzyme subtilisin Carlsberg.

EXAMPLE 1

Transesterification of N-Acetyl-L-phenylalanine Ethyl Ester with Propanol Using subtilisin Carlsberg Enzyme A mixture was prepared containing 0.0285 gram (0.000121 mole) of N-acetyl-L-phenylalanine ethyl ester, 0.0164 g (0.000061 mole) of nonadecane, and 0.75 mL of propanol in 9.25 mL of octane. A 2 mL aliquot of this solution was placed in a 5 mL vial. To the vial were added 0.0012 g of subtilisin Carlsberg enzyme powder and 12 $\mu$L of water. This mixture was shaken at a temperature of 40–42° C. Periodically, small samples were removed and analyzed by gas chromatography. After 60 minutes, analysis indicated that 0.00486 gram of N-acetyl-L-phenylalanine propyl ester had been formed. Prior to running this reaction the subtilisin Carlsberg enzyme powder had been dissolved in 20 mM potassium phosphate buffer solution at a concentration of 5 mg/mL. After adjusting the pH to 7.8 with potassium hydroxide, the solution was lyophilized by being frozen in liquid nitrogen and then putting the sample under a vacuum of 2.67 Pa at −45° C. for 30 hours.

EXAMPLE 2

Preparation of Carrageenan Gel Beads Containing Embedded subtilisin Carlsberg Enzyme Carrageenan gel beads containing subtilisin Carlsberg enzyme were prepared by the procedure described in U.S. Pat. No. 5,662,840. A solution containing 2.5 wt % carrageenan, 0.2 wt % potassium chloride, 0.1 wt % calcium chloride, and 0.1 wt % sodium benzoate in deionized water was prepared. The resulting solution was heated and maintained at a temperature of approximately 92–93° C. with stirring to prevent gelation. This solution was then pumped through heated tubing to a high pressure spray head at a flow rate of 24 mL/minute. Just prior to reaching the spray head, a cold solution of 25 mg of subtilisin Carlsberg enzyme/mL of 20 mM potassium phosphate buffer, the pH of which had been adjusted to 7.8 with potassium hydroxide, was injected into the carrageenan solution at a rate of 6 mL/minute. This created a solution containing 2 wt % carrageenan and 5 mg of subtilisin Carlsberg/mL. Simultaneously, a stream of air was passed through the spray head at a pressure of 51.7 kPa (75 psi), impinging on the carrageenan/enzyme solution as it left the spray head and atomizing the aqueous solution. The pressure differential instantly dispersed the carrageenan/enzyme solution into droplets which immediately cooled and solidified into beads having an average diameter of approximately 20 microns. The resulting carrageenan beads containing subtilisin Carlsberg enzyme were then lyophilized and stored under anhydrous conditions for later use. Calculations determined that 5 mg of enzyme were contained in 25 mg of dried beads.

EXAMPLE 3

Transesterification of N-Acetyl-L-phenylalanine Ethyl Ester with Propanol Using subtilisin Carlsberg Enzyme Embedded in Carrageenan Beads A mixture was prepared containing 0.0280 gram (0.000119 mole) of N-acetyl-L-phenylalanine ethyl ester, 0.0145 g (0.000061 mole) of nonadecane, and 0.75 mL of propanol in 9.25 mL of octane. A 2 mL aliquot of this solution was placed in a 5 mL vial. To 5 mg of the lyophilized beads produced in Example 2 was added 250 $\mu$L of water to rehydrate the beads to their condition before lyophilization. These rehydrated beads were then added to the reaction vial which was shaken at 40° C. Periodically, small samples of the reaction mixture were removed and analyzed by gas chromatography. After 60 minutes, analysis indicated that 0.00199 gram of N-acetyl-L-phenylalanine propyl ester had been formed. Carrageenan beads containing subtilisin Carlsberg enzyme have been shown to absorb 25% of the N-acetyl-L-phenylalanine ethyl ester, reducing the amount of this starting material that was available for transesterification in the original mixture to 0.0042 gram.

EXAMPLE 4

Preparation of subtilisin Enzyme Solution

A 20 mM potassium phosphate buffer solution was prepared and adjusted to a pH of 7.8 with potassium hydroxide. To 55.5 mL of the buffered solution was added 0.2767 gram of subtilisin Carlsberg enzyme powder. The resulting solution contained 0.49 wt % of the enzyme. This enzyme solution was stirred in a refrigerator for 30 minutes prior to being used. For longer term storage the solution was lyophilized as described in Example 1 and then reconstituted for use as needed.

EXAMPLE 5

Preparation of Carrageenan Beads Containing Imbibed subtilisin Carlsberg Enzyme Carrageenan beads having a content of 2 wt % carrageenan, but no enzyme, were made according to the process of Example 2. These beads were lyophilized in the manner described in Example 1. Beads weighing 0.7515 gram were added to 55.5 mL of the enzyme solution prepared in Example 4, and the mixture was stirred in a refrigerator for two hours. At the conclusion of this period, the mixture was transferred to a centrifuge tube in which it was centrifuged at 4000 rpm at 10° C. for 15 minutes. During centrifugation, the carrageenan formed a sticky pellet, allowing 30.7 mL of supernatant liquid to be decanted. The carrageenan pellet was transferred to a freeze-drying bottle in which it was lyophilized. The supernatant liquid was analyzed by ultraviolet spectrophotometry at 280 nanometers according to the method of Pantoliano et al. (*Biochemistry*, 28, 7205 (1989)). The enzyme concentration was found to be 0.46 wt %. From the volume of supernatant, the solution imbibed by the dried carrageenan beads had been sufficient to restore the beads to a 3 wt % carrageenan gel containing 0.173 gram of enzyme per gram of carrageenan. These beads were then lyophilized as described above and stored for later use.

EXAMPLE 6

Transesterification of N-Acetyl-L-phenylalanine Ethyl Ester with Propanol Using subtilisin Carlsberg Enzyme Imbibed in Carrageenan Beads A mixture was prepared containing 0.0282 gram (0.000120 mole) of N-acetyl-L-phenylalanine ethyl ester, 0.0170 gram (0.000063 mole) of nonadecane, and 0.75 mL of propanol in 9.25 mL of octane. A 2 mL aliquot of this solution was placed in a 5 mL vial. To 5.8 mg of the lyophilized beads produced in Example 5 was added 193 μL of water to rehydrate the beads to their condition before lyophilization. These rehydrated beads were then added to the reaction vial which was shaken at 40° C. Periodically, small samples of the reaction mixture were removed and analyzed by gas chromatography. After 60 minutes, analysis indicated that 0.00268 gram of N-acetyl-L-phenylalanine propyl ester had been formed. Carrageenan beads containing subtilisin Carlsberg enzyme have been shown to absorb 25% of the N-acetyl-L-phenylalanine ethyl ester, reducing the amount of this starting material that was available for transesterification in the original mixture to 0.00423 gram.

What is claimed:

1. Hydrocolloid gel beads comprising a hydrocolloid and a catalytically effective amount of an immobilized enzyme for use in non-aqueous enzymatic reactions made by the process comprising:
    (a) dehydrating hydrocolloid gel beads having an average particle size in the range of 5 microns to 150 microns in diameter and having a network structure capable of swelling in aqueous media;
    (b) imbibing into the dehydrated gel beads an aqueous solution of the enzyme to form imbibed gel beads; and
    (c) recovering the imbibed gel beads in which a catalytically effective amount of enzyme has been immobilized.

2. The hydrocolloid gel beads of claim 1 in which the hydrocolloid is carrageenan.

3. The hydrocolloid gel beads of claim 1 in which the enzyme is selected from the group consisting of oxidoreductases, transferases, hydrolases, lyases, isomerases, ligases, decarboxylases, carboxylases, aldolases, thiolases, and synthases.

4. The hydrocolloid gel beads of claim 1 in which the enzyme is subtilisin Carlsberg.

5. The hydrocolloid gel beads of claim 1 in which dehydrating the hydrocolloid gel beads comprises lyophilization.

6. The hydrocolloid gel beads of claim 1 in which the method additionally comprises, after step (b) and before step (c), the step of dehydrating the imbibed gel beads.

7. The hydrocolloid gel beads of claim 6 in which the hydrocolloid is carrageenan.

8. The hydrocolloid gel beads of claim 6 in which dehydrating the imbibed beads comprises lyophilization.

9. A method for immobilizing an enzyme for use in non-aqueous enzymatic reactions comprising:
    (a) dehydrating hydrocolloid gel beads having an average particle size in the range of 5 microns to 150 microns in diameter and having a network structure capable of swelling in aqueous media;
    (b) imbibing into the dehydrated hydrocolloid gel beads an aqueous solution of the enzyme to form imbibed gel beads; and
    (c) recovering the imbibed gel beads in which a catalytically effective amount of enzyme has been immobilized.

10. The method of claim 9 in which the hydrocolloid is carrageenan.

11. The method of claim 9 in which the hydrocolloid is kappa carrageenan.

12. The method of claim 9 in which the enzyme is selected from the group consisting of oxidoreductases, transferases, hydrolases, lyases, isomerases, ligases, decarboxylases, carboxylases, aldolases, thiolases, and synthases.

13. The method of claim 12 in which the enzyme is subtilisin Carlsberg.

14. The method of claim 9 in which the hydrocolloid is carrageenan, the enzyme is subtilisin Carlsberg, and the aqueous solution of enzyme contains in the range of 0.05 to 40 wt % enzyme.

15. The method of claim 9 in which dehydrating the hydrocolloid gel beads comprises lyophilization.

16. The method of claim 9 additionally comprising, after step (b) and before step (c), the step of dehydrating the imbibed gel beads.

17. The method of claim 16 in which the hydrocolloid is carrageenan.

18. The method of claim 16 in which dehydrating the imbibed beads comprises lyophilization.

* * * * *